US009682869B2

(12) United States Patent
Tooley et al.

(10) Patent No.: US 9,682,869 B2
(45) Date of Patent: Jun. 20, 2017

(54) PARTICULATE TITANIUM DIOXIDE

(75) Inventors: Ian Robert Tooley, Warrington (GB); Robert Michael Sayer, Billinge (GB); Paul Martin Staniland, Altrincham (GB)

(73) Assignee: Croda International PLC, East Yorkshire (GB)

( * ) Notice: Subject to any disclaimer, the term of this patent is extended or adjusted under 35 U.S.C. 154(b) by 0 days.

(21) Appl. No.: 13/515,208

(22) PCT Filed: Dec. 22, 2010

(86) PCT No.: PCT/GB2010/002308
§ 371 (c)(1),
(2), (4) Date: Jun. 11, 2012

(87) PCT Pub. No.: WO2011/077084
PCT Pub. Date: Jun. 30, 2011

(65) Prior Publication Data
US 2012/0294914 A1   Nov. 22, 2012

(30) Foreign Application Priority Data

Dec. 23, 2009   (GB) .................................. 0922552.5

(51) Int. Cl.
| | | |
|---|---|---|
| *C01G 23/047* | (2006.01) | |
| *A61K 8/02* | (2006.01) | |
| *A61K 8/29* | (2006.01) | |
| *A61Q 17/04* | (2006.01) | |
| *B82Y 30/00* | (2011.01) | |
| *C01G 23/08* | (2006.01) | |
| *C01G 23/053* | (2006.01) | |

(52) U.S. Cl.
CPC .......... *C01G 23/047* (2013.01); *A61K 8/0241* (2013.01); *A61K 8/29* (2013.01); *A61Q 17/04* (2013.01); *B82Y 30/00* (2013.01); *C01G 23/0536* (2013.01); *C01G 23/08* (2013.01); *A61K 2800/412* (2013.01); *C01P 2002/84* (2013.01); *C01P 2004/54* (2013.01); *C01P 2004/62* (2013.01); *C01P 2004/64* (2013.01); *C01P 2006/11* (2013.01); *C01P 2006/60* (2013.01); *C01P 2006/62* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 5,605,652 A | 2/1997 | Tapley | |
| 5,973,175 A * | 10/1999 | Bruno ...................... A61K 8/19 | |
| | | | 534/15 |
| 7,220,305 B2 * | 5/2007 | Dransfield et al. ........... 106/401 |
| 2006/0159596 A1 * | 7/2006 | De La Veaux et al. ...... 422/151 |
| 2008/0153922 A1 * | 6/2008 | Noguchi ............... C09C 1/0015 |
| | | | 514/769 |
| 2009/0130577 A1 * | 5/2009 | Joo et al. ........................ 430/96 |
| 2009/0263314 A1 | 10/2009 | Chung | |

FOREIGN PATENT DOCUMENTS

| | | |
|---|---|---|
| EP | 0341703 | 11/1989 |
| EP | 0535972 A1 | 4/1993 |
| EP | 0599492 | 6/1994 |
| EP | 2085142 A1 | 8/2009 |
| EP | 1954767 B1 | 8/2012 |
| JP | 04-055403 | 2/1992 |
| JP | 05-201844 | 8/1993 |
| JP | 08-217654 | 8/1996 |
| JP | 2004-501858 | 1/2004 |
| JP | 2004-210646 | 7/2004 |
| JP | 2006-527160 | 11/2006 |
| JP | 2007-529483 | 10/2007 |
| JP | 2009-513483 | 4/2009 |
| JP | 2010-006629 | 1/2010 |
| WO | WO 2007/048057 | 4/2007 |
| WO | WO 2008/056744 | 5/2008 |

OTHER PUBLICATIONS

Ferrero, L., et al., "Importance of Substrate Roughness for In Vitro Sun Protection Assessmen1", 2006, IFSCC, pp. 1-13.*
Ke, Y.C., et al., "Polymer-Layered Silicate and Silica Nanocomposites", Elsevier, 2005, pp. 220.*
International Search Report dated Mar. 17, 2011 for PCT/GB2010/002308.
http://www.brookhaveninstruments.com/pdf/product_selection/BI-XDC.pdf, retrieved Nov. 30, 2014.
English translation of Examination Report mailed Apr. 22, 2014 in corresponding Japanese Application No. 2012-545430.

* cited by examiner

*Primary Examiner* — Michael G Hartley
*Assistant Examiner* — Lance Rider
(74) *Attorney, Agent, or Firm* — RatnerPrestia

(57) ABSTRACT

A particulate titanium dioxide has a median volume particle diameter of greater than 70 nm. The titanium dioxide can be produced by calcining precursor particles. The titanium dioxide has enhanced UVA efficacy. The particulate titanium dioxide can be used to form dispersions. The particulate titanium dioxide or dispersions can be used to produce sunscreen products having a UV protection which is at least one third of the label SPF value.

21 Claims, No Drawings

PARTICULATE TITANIUM DIOXIDE

CROSS REFERENCE TO RELATED APPLICATION

This application is the National Phase application of International Application No. PCT/GB2010/002308, filed Dec. 22, 2010, which designates the United States and was published in English. This application, in its entirety, is incorporated herein by reference.

FIELD OF INVENTION

The present invention relates to titanium dioxide particles and a method of making thereof, a dispersion made therefrom, and in particular to the use in an end-use product.

BACKGROUND

Titanium dioxide has been employed as an attenuator of ultraviolet light in a wide range of applications such as sunscreens, organic resins, films and coatings.

It is well known that UVA radiation contributes primarily to premature skin ageing, whilst UVB radiation is the predominant cause of skin cancer. Currently, almost all commercially available titanium dioxide products attenuate predominantly in the UVB region. Whilst these titanium dioxide products may give some UVA attenuation, many final end-use sunscreen products need to incorporate inorganic UVA absorbers such as zinc oxide and/or organic UVA absorbers such as butyl methoxydibenzoylmethane (avobenzone) in order to obtain the required broad spectrum UV protection. The demand for sunscreen products with improved UVA efficacy and a high UVA/UVB ratio has increased recently with the new European Union Commission requirements for all sunscreen products to have a UVA protection which is at least one third of the label SPF value.

In addition, the demand for "inorganic only" sunscreens has increased in recent years, due to concerns over the toxicity of various organic UV absorbers, and the "yellowing" impact some organic UV absorbers have on inorganic sunscreens. The requirement for an alternative to zinc oxide has also developed due to legislation restricting the use of zinc oxide, and the relatively low UV attenuation and/or transparency of zinc oxide.

Thus, there is a need for a particulate titanium dioxide which exhibits effective UVB absorption properties, but also has a high UVA efficacy, and acceptable aesthetics when applied to the skin, e.g. transparency and/or skin feel.

SUMMARY OF THE INVENTION

We have now surprisingly discovered an improved titanium dioxide, which overcomes or significantly reduces at least one of the aforementioned problems.

Accordingly, the present invention provides a particulate titanium dioxide having a median volume particle diameter of greater than 70 nm.

The invention further provides a particulate titanium dioxide having an $E_{524}$ of less than 9 l/g/cm, an $E_{360}$ of 25 to 50 l/g/cm, and an $E_{360}/E_{308}$ ratio of 0.5 to 1.0.

The invention yet further provides a dispersion comprising particulate titanium dioxide having a median volume particle diameter of greater than 70 nm and/or an $E_{524}$ of less than 9 l/g/cm, an $E_{360}$ of 25 to 50 l/g/cm, and an $E_{360}/E_{308}$ ratio of 0.5 to 1.0.

The invention still further provides a method of producing particulate titanium dioxide which comprises (i) forming precursor titanium dioxide particles having a mean length of 40 to 100 nm and/or a mean width of 3 to 25 nm, and (ii) calcining the precursor particles.

The invention even further provides a sunscreen product comprising (i) particulate titanium dioxide having (a) a median volume particle diameter of greater than 70 nm, and/or (b) an $E_{524}$ of less than 9 l/g/cm, an $E_{360}$ of 25 to 50 l/g/cm, and an $E_{360}/E_{308}$ ratio of 0.5 to 1.0; and/or (ii) a dispersion comprising particulate titanium dioxide having (a) a median volume particle diameter of greater than 70 nm, and/or (b) an $E_{524}$ of less than 9 l/g/cm, an $E_{350}$ of 25 to 50 l/g/cm, and an $E_{360}/E_{308}$ ratio of 0.5 to 1.0; and/or (iii) particulate titanium dioxide which is produced by (a) forming precursor titanium dioxide particles having a mean length of 40 to 100 nm and/or a mean width of 3 to 25 nm, and (b) calcining the precursor particles.

The titanium dioxide particles according to the present invention preferably comprise anatase and/or rutile crystal form. The titanium dioxide in the particles suitably comprises a major portion of rutile, preferably greater than 70%, more preferably greater than 80%, particularly greater than 90%, and especially greater than 95% and up to 100% by weight of rutile.

The particles may be prepared by standard procedures, such as using the chloride process, or by the sulphate process, or by the hydrolysis of an appropriate titanium compound such as titanium oxydichloride or an organic or inorganic titanate, or by oxidation of an oxidisable titanium compound, e.g. in the vapour state.

In one embodiment, the titanium dioxide particles may be doped with a dopant metal selected from the group consisting of aluminium, chromium, cobalt, copper, gallium, iron, lead, manganese, nickel, silver, tin, vanadium, zinc, zirconium, and combinations thereof. The dopant is preferably selected from the group consisting of chromium, cobalt, copper, iron, manganese, nickel, silver, and vanadium, more preferably from manganese and vanadium, particularly manganese, and especially in the 2+ and/or 3+ state.

Doping can be performed by normal methods known in the art. Doping is preferably achieved by co-precipitation of titanium dioxide and a soluble dopant complex such as manganese chloride or manganese acetate. Alternatively, doping can be performed by a baking technique by heating a titanium complex in the presence of a dopant complex, e.g. manganese nitrate, at a temperature of greater than 500° C. and normally up to 1,000° C. Dopants can also be added by oxidizing a mixture containing a titanium complex and dopant complex, e.g. manganese acetate, such as by spraying the mixture through a spray atomizer into an oxidation chamber.

Doped titanium dioxide particles preferably comprise in the range from 0.01 to 3%, more preferably 0.05 to 2%, particularly 0.1 to 1%, and especially 0.5 to 0.7% by weight of dopant metal, preferably manganese, based on the weight of titanium dioxide.

In one embodiment, initial or precursor titanium dioxide particles are prepared, for example, by the hydrolysis of a titanium compound, particularly of titanium oxydichloride, and these precursor particles are then subjected to a calcination process in order to obtain titanium dioxide particles according to the present invention.

The precursor titanium dioxide particles preferably comprise a rutile content as hereinbefore described. In addition, the precursor titanium dioxide particles preferably comprise less than 10%, more preferably less than 5%, and particularly less than 2% by weight of amorphous titanium dioxide. The remaining titanium dioxide (i.e. up to 100%) is in crystalline form. The titanium dioxide in the precursor particles preferably is substantially all in crystalline form.

The individual precursor titanium dioxide particles are suitably acicular in shape and have a long axis (maximum dimension or length) and short axis (minimum dimension or width). The third axis of the particles (or depth) is preferably approximately the same dimensions as the width.

The mean length by number of the precursor titanium dioxide particles is suitably in the range from 40 to 100 nm, preferably 45 to 90 nm, more preferably 50 to 80 nm, particularly 55 to 70 nm, and especially 60 to 65 nm. The mean width by number of the particles is suitably in the range from 3 to 25 nm, preferably 6 to 20 nm, more preferably 9 to 18 nm, particularly 12 to 17 nm, and especially 14 to 16 nm. The precursor titanium dioxide particles preferably have a mean aspect ratio $d_1:d_2$ (where $d_1$ and $d_2$, respectively, are the length and width of the particle) in the range from 2 to 8:1, more preferably 3 to 6.5:1, particularly 4 to 6:1, and especially 4.5 to 5.5:1. The size of the precursor particles can be determined, as herein described, by measuring the length and width of particles selected from a photographic image obtained by using a transmission electron microscope.

The precursor titanium dioxide particles suitably have a mean crystal size (measured by X-ray diffraction as herein described) in the range from 5 to 20 nm, preferably 6 to 15 nm, more preferably 7 to 12 nm, particularly 8 to 11 nm, and especially 9 to 10 nm.

The size distribution of the crystal size of the precursor titanium dioxide particles can be important, and suitably at least 30%, preferably at least 40%, more preferably at least 50%, particularly at least 60%, and especially at least 70% by weight of the titanium dioxide particles have a crystal size within one or more of the above preferred ranges for the mean crystal size.

The precursor titanium dioxide particles are preferably calcined at a temperature in the range from 450 to 850° C., more preferably 500 to 800° C., particularly 550 to 750° C., and especially 600 to 700° C. The precursor titanium dioxide particles are preferably calcined for a time period in the range from 1 to 15 hours. For small or laboratory-scale production, e.g. for quantities of up to and including 20 Kg, the precursor titanium dioxide particles are preferably calcined for 1 to 5 hours, more preferably 1.5 to 4 hours, and particularly 2 to 3 hours. For plant-scale production, e.g. for quantities greater than 20 Kg, the precursor titanium dioxide particles are preferably calcined for 4 to 15 hours, more preferably 4.5 to 12 hours, and particularly 5 to 9 hours.

The precursor titanium dioxide particles may be dried prior to calcination such that they contain less than 5% by weight of water, but in one embodiment a pre-drying stage is not employed. In this embodiment, the precursor particles, which are subjected to the calcination process, preferably comprise in the range from 40 to 75%, more preferably 50 to 70%, particularly 55 to 65%, and especially about 60% by weight of water based on the total weight of particles and water.

In one embodiment of the present invention, the titanium dioxide particles are coated with an inorganic and/or organic coating. Doped titanium dioxide particles may be uncoated, i.e. consist essentially of titanium dioxide and dopant.

The inorganic coating is preferably an oxide of aluminium, zirconium or silicon, or mixtures thereof such as alumina and silica. The amount of inorganic coating, suitably alumina and/or silica, is preferably in the range from 1 to 20%, more preferably 2 to 10%, particularly 3 to 6%, and especially 3 to 4% by weight, based on the weight of titanium dioxide core particles.

In one embodiment of the invention, the titanium dioxide particles are hydrophobic. The hydrophobicity of the titanium dioxide can be determined by pressing a disc of titanium dioxide powder, and measuring the contact angle of a drop of water placed thereon, by standard techniques known in the art. The contact angle of a hydrophobic titanium dioxide is preferably greater than 50°.

The titanium dioxide particles can be coated in order to render them hydrophobic. Suitable coating materials are water-repellent, preferably organic, and include fatty acids, preferably fatty acids containing 10 to 20 carbon atoms, such as lauric acid, stearic acid and isostearic acid, salts of the above fatty acids such as sodium, potassium and/or aluminium salts, fatty alcohols, such as stearyl alcohol, and silicones such as polydimethylsiloxane and substituted polydimethylsiloxanes, and reactive silicones such as methylhydrosiloxane and polymers and copolymers thereof. Stearic acid and/or salt thereof is particularly preferred. Generally, the particles are treated with up to 20%, suitably in the range from 1 to 15%, more preferably 2 to 10%, particularly 3 to 7%, and especially 4 to 5% by weight of organic material, preferably fatty acid, based on the weight of the titanium dioxide core particles.

In one embodiment of the invention, the titanium dioxide particles are coated with both an inorganic coating, preferably alumina and/or silica; and an organic coating, either sequentially or as a mixture. It is preferred that the inorganic coating is applied first followed by the organic coating, preferably fatty acid and/or salt thereof. Thus in one embodiment, titanium dioxide particles comprise, based on the total weight of the particles, (i) in the range from 80 to 96%, more preferably 85 to 95%, particularly 88 to 94%, and especially 91 to 93% by weight of titanium dioxide, (ii) in the range from 1 to 8%, more preferably 1.5 to 6%, particularly 2 to 5%, and especially 2.5 to 4% by weight of alumina and/or silica coating, and (iii) in the range from 2 to 12%, more preferably 2.5 to 9%, particularly 3 to 7%, and especially 3.5 to 5% by weight of organic coating, preferably fatty acid and/or salt thereof.

The titanium dioxide particles may be coated prior to, or after any calcination stage. In a preferred embodiment, any coating is applied to the calcined particles. Thus, it is preferred that uncoated precursor titanium dioxide particles are subjected to the calcination process described herein.

In one embodiment, the titanium dioxide particles are coated in-situ, during the formation of a dispersion according to the present invention. Such coating may be applied by adding coating materials to the dispersion mixture before the milling process as described herein. Examples of materials which are suitable for the in-situ coating process are isostearic acid, oleth-3 phosphate, octyl/decyl phosphate, ceteleth-5 phosphate, PPG-5-ceteth-10 phosphate, trideceth-5 phosphate, dobanol C12-C15 phosphate, C9-C15 alkyl phosphate, glyceryl triacetate, sorbitan laurate, sorbitan isostearate, sodium lauryl sulfate, sodium methyl cocoyl taurate, and mixtures thereof. Isostearic acid is one preferred coating material.

The individual, preferably calcined, titanium dioxide particles according to the present invention suitably have a mean aspect ratio $d_1:d_2$ (where $d_1$ and $d_2$, respectively, are the length and width of the particle) in the range from 1.0 to 2.5:1, preferably 1.2 to 2.0:1, more preferably 1.3 to 1.8:1, particularly 1.4 to 1.6:1, and especially 1.45 to 1.55:1. The mean length by number of the titanium dioxide particles is suitably in the range from 30 to 75 nm, preferably 36 to 68 nm, more preferably 42 to 62 nm, particularly 47 to 57 nm, and especially 50 to 54 nm. The mean width by number of the particles is suitably in the range from 20 to 55 nm, preferably 25 to 48 nm, more preferably 28 to 42 nm, particularly 31 to 38 nm, and especially 33 to 36 nm.

The size of the titanium dioxide particles can be determined, as herein described, by measuring the length and width of particles selected from a photographic image obtained by using a transmission electron microscope.

The titanium dioxide particles according to the present invention suitably have a mean crystal size (measured by X-ray diffraction as herein described) in the range from 15 to 45 nm, preferably 20 to 40 nm, more preferably 25 to 35 nm, particularly 28 to 33 nm, and especially 30 to 31 nm.

The size distribution of the crystal size of the titanium dioxide particles can be important, and suitably at least 30%, preferably at least 40%, more preferably at least 50%, particularly at least 60%, and especially at least 70% by weight of the titanium dioxide particles have a crystal size within one or more of the above preferred ranges for the mean crystal size.

The particulate titanium dioxide according to the present invention may be in the form of a free-flowing powder. A powder having the required particle size may be produced by milling processes known in the art. The final milling stage of the titanium dioxide is suitably carried out in dry, gas-borne conditions to reduce aggregation. A fluid energy mill can be used in which the aggregated titanium dioxide powder is continuously injected into highly turbulent conditions in a confined chamber where multiple, high energy collisions occur with the walls of the chamber and/or between the aggregates. The milled powder is then carried into a cyclone and/or bag filter for recovery. The fluid used in the energy mill may be any gas, cold or heated, or superheated dry steam.

The particulate titanium dioxide may be formed into a slurry, or preferably a liquid dispersion, in any suitable aqueous or organic liquid medium. By liquid is meant liquid at ambient temperature (e.g. 25° C.), and by dispersion is meant a true dispersion, i.e. where the solid particles are stable to aggregation. The particles in the dispersion are relatively uniformly dispersed and resistant to settling out on standing, but if some settling out does occur, the particles can be easily redispersed by simple agitation.

Alternatively, the particulate titanium dioxide may be in the form of a lotion or cream of a solid and/or semi-solid dispersion. Suitable solid or semi-solid dispersions may contain, for example, in the range from 50 to 90%, preferably 60 to 85% by weight of particulate titanium dioxide, together with any one or more of the liquid media disclosed herein, or a high molecular weight polymeric material, such as a wax, e.g. glyceryl monostearate.

For use in a sunscreen product, cosmetically acceptable materials are preferred as the liquid medium. The liquid medium may be water, or an organic medium such as a liquid, e.g. vegetable, oil, fatty acid glyceride, fatty acid ester and/or fatty alcohol. One suitable organic medium is a siloxane fluid, especially a cyclic oligomeric dialkylsiloxane, such as the cyclic pentamer of dimethylsiloxane known as cyclomethicone. Alternative fluids include dimethylsiloxane linear oligomers or polymers having a suitable fluidity and phenyltris(trimethylsiloxy)silane (also known as phenyltrimethicone).

Examples of other suitable organic media include non-polar materials such as C13-C14 isoparaffin, isohexadecane, paraffinum liquidum (mineral oil), squalane, squalene, hydrogenated polyisobutene, and polydecene; and polar materials such as C12-C15 alkyl benzoate, caprylic/capric triglyceride, cetearyl isononanoate, ethylhexyl isostearate, ethylhexyl palmitate, isononyl isononanoate, isopropyl isostearate, isopropyl myristate, isostearyl isostearate, isostearyl neopentanoate, octyldodecanol, pentaerythrityl tetraisostearate, PPG-15 stearyl ether, triethylhexyl triglyceride, dicaprylyl carbonate, ethylhexyl stearate, helianthus annus (sunflower) seed oil, isopropyl palmitate, and octyldodecyl neopentanoate, triethylhexanoin, ethylhexyl cocoate, propylene glycol isostearate, glyceryl isostearate, triisostearin, diethoxyethyl succinate, caprylyl eicosanoate, ethylhexyl hydroxystearate, lauryl lactate, butyl stearate, diisobutyl adipate, diisopropyl adipate, ethyl oleate, isocetyl stearate, propylene glycol dicaprylate/dicaprate, pentaerythrityl tetracaprylate/tetracaprate, oleyl oleate, propylene glycol isoceteth-3 acetate, PPG-3 benzyl ether myristate, cetearyl ethylhexanoate, ethylhexyl pelargonate, PPG-2 myristyl ether propionate, C14-18 alkyl ethylhexanoate, and mixtures thereof.

The dispersion according to the present invention may also contain a dispersing agent in order to improve the properties thereof. The dispersing agent is suitably present in the range from 1 to 30%, preferably 4 to 20%, more preferably 6 to 15%, particularly 8 to 12%, and especially 9 to 11% by weight based on the total weight of titanium dioxide particles.

Suitable dispersing agents include substituted carboxylic acids, soap bases and polyhydroxy acids. Typically the dispersing agent can be one having a formula R.CO.AX in which A is a divalent atom such as O, or a divalent bridging group. X can be hydrogen or a metal cation, or a primary, secondary or tertiary amino group or a salt thereof with an acid or a quaternary ammonium salt group. R may be the residue of a polyester chain which together with the —CO— group is derived from a hydroxy carboxylic acid of the formula HO—R'—COOH. As examples of typical dispersing agents are those based on ricinoleic acid, hydroxystearic acid, hydrogenated castor oil fatty acid which contains in addition to 12-hydroxystearic acid small amounts of stearic acid and palmitic acid. Dispersing agents based on one or more polyesters or salts of a hydroxycarboxylic acid and a carboxylic acid free of hydroxy groups can also be used. Compounds of various molecular weights can be used.

Other suitable dispersing agents are those monoesters of fatty acid alkanolamides and carboxylic acids and their salts. Suitable alkanolamides, for example, include those based on ethanolamine, propanolamine or aminoethyl ethanolamine. The dispersing agent can be one of those commercially referred to as a hyper dispersant. Polyhydroxystearic acid is a particularly preferred dispersing agent in organic media.

Suitable dispersing agents for use in an aqueous medium include a polymeric acrylic acid or a salt thereof. Partially or fully neutralized salts are usable e.g. the alkali metal salts and ammonium salts. Examples of dispersing agents are polyacrylic acids, substituted acrylic acid polymers, acrylic copolymers, sodium and/or ammonium salts of polyacrylic acids and sodium and/or ammonium salts of acrylic copolymers. Such dispersing agents are typified by polyacrylic acid itself and sodium or ammonium salts thereof as well as copolymers of an acrylic acid with other suitable monomers such as a sulphonic acid derivative such as 2-acrylamido 2-methyl propane sulphonic acid. Comonomers polymerisable with the acrylic or a substituted acrylic acid can also be one containing a carboxyl grouping. Usually the dispersing agents for use in an aqueous medium have a molecular weight in the range from 1,000 to 10,000, and are preferably substantially linear molecules. Materials such as sodium citrate may also be used as a co-dispersant.

An advantage of the present invention is that dispersions, particularly liquid, can be produced which suitably contain at least 30%, preferably at least 40%, more preferably at least 50%, particularly at least 55%, especially at least 60%, and generally up to 65%, by weight of titanium dioxide particles based on the total weight of the dispersion.

The particulate titanium dioxide, preferably calcined, according to the present invention suitably has a median volume particle diameter (equivalent spherical diameter corresponding to 50% of the volume of all the particles, read on the cumulative distribution curve relating volume % to the diameter of the particles—often referred to as the "D(v, 0.5)" value)) in dispersion, measured as herein described, of greater than 70 nm, preferably in the range from 85 to 175 nm, more preferably 100 to 160 nm, particularly 115 to 150 nm, and especially 125 to 140 nm.

The size distribution of the titanium dioxide particles can also be an important parameter in obtaining an end-use product having the required properties. In a preferred embodiment suitably less than 10% by volume of titanium dioxide particles have a volume diameter of more than 40 nm, preferably more than 35 nm, more preferably more than 30 nm, particularly more than 25 nm, and especially more than 20 nm below the median volume particle diameter. In addition, suitably less than 16% by volume of titanium dioxide particles have a volume diameter of more than 35 nm, preferably more than 30 nm, more preferably more than 25 nm, particularly more than 20 nm, and especially more than 15 nm below the median volume particle diameter. Further, suitably less than 30% by volume of titanium dioxide particles have a volume diameter of more than 25 nm, preferably more than 20 nm, more preferably more than 15 nm, particularly more than 11 nm, and especially more than 7 nm below the median volume particle diameter.

Also, suitably more than 90% by volume of titanium dioxide particles have a volume diameter of less than 110 nm, preferably less than 90 nm, more preferably less than 75 nm, particularly less than 60 nm, and especially less than 50 nm above the median volume particle diameter. In addition, suitably more than 84% by volume of titanium dioxide particles have a volume diameter of less than 75 nm, preferably less than 60 nm, more preferably less than 50 nm, particularly less than 40 nm, and especially less than 30 nm above the median volume particle diameter. Further, suitably more than 70% by volume of titanium dioxide particles have a volume diameter of less than 35 nm, preferably less than 25 nm, more preferably less than 20 nm, particularly less than 15 nm, and especially less than 10 nm above the median volume particle diameter.

The dispersion particle size of the titanium dioxide particles according to the present invention may be measured by techniques based on sedimentation analysis. The median volume particle diameter may be determined by plotting a cumulative distribution curve representing the percentage of particle volume below chosen particle sizes and measuring the 50th percentile. The median volume particle diameter and particle size distribution of the titanium dioxide particles is suitably measured by forming a dispersion of titanium dioxide particles and using a Brookhaven particle sizer, both as described herein.

The titanium dioxide particles suitably have a BET specific surface area, measured as described herein, in the range from 20 to 45, preferably 22 to 40, more preferably 24 to 35, particularly 26 to 31, and especially 27 to 29 $m^2 g^{-1}$.

The titanium dioxide particles according to the present invention are transparent, suitably having an extinction coefficient at 524 nm ($E_{524}$), measured as herein described, of less than 9, preferably in the range from 1 to 8, more preferably 3 to 7, particularly 4 to 6.5, and especially 5 to 6 l/g/cm.

The titanium dioxide particles exhibit effective UV absorption, suitably having an extinction coefficient at 360 nm ($E_{360}$), measured as herein described, of greater than 20, preferably in the range from 25 to 50, more preferably 30 to 46, particularly 33 to 43, and especially 35 to 40 l/g/cm. The titanium dioxide particles also suitably have an extinction coefficient at 308 nm ($E_{308}$), measured as herein described, of greater than 30, preferably in the range from 35 to 65, more preferably 40 to 58, particularly 45 to 53, and especially 47 to 50 l/g/cm.

The titanium dioxide particles suitably have a maximum extinction coefficient E(max), measured as herein described, of greater than 30, preferably in the range from 37 to 70, more preferably 43 to 60, particularly 47 to 55, and especially 49 to 53 l/g/cm.

The titanium dioxide particles suitably have a λ(max), measured as herein described, in the range from 305 to 345, preferably 310 to 340, more preferably 315 to 335, particularly 320 to 330, and especially 325 to 327 nm.

In one embodiment, the titanium dioxide particles suitably have an $E_{360}/E_{524}$ ratio of greater than 3.5, preferably in the range from 4.5 to 12, more preferably 5 to 9, particularly 5.5 to 6.5, and especially 5.8 to 6.2.

The titanium dioxide particles suitably have an $E_{308}/E_{524}$ ratio of greater than 4, preferably in the range from 5 to 15, more preferably 6 to 12, particularly 7 to 9, and especially 7.5 to 8.5.

The titanium dioxide particles suitably have an $E_{360}/E_{308}$ ratio in the range from 0.5 to 1.0, preferably 0.6 to 0.95, more preferably 0.65 to 0.9, particularly 0.7 to 0.85, and especially 0.75 to 0.8.

One feature of the present invention is that the titanium dioxide particles can have significantly reduced photoactivity, suitably having a photogreying index, measured as herein described, of less than 5, preferably in the range from 0.05 to 3, more preferably 0.1 to 1, particularly 0.2 to 0.5, and especially 0.25 to 0.35.

The titanium dioxide particles suitably exhibit a change in whiteness ΔL of a sunscreen product containing the particles, measured as herein described, of less than 30, preferably in the range from 1 to 25, more preferably 5 to 20, particularly 10 to 17, and especially 12 to 15.

A composition, preferably an end-use sunscreen product, containing the titanium dioxide particles according to the present invention preferably comprises greater than 0.5%, more preferably in the range from 1 to 25%, particularly 3 to 20%, and especially 5 to 15% by weight based on the total weight of the composition, of titanium dioxide particles described herein.

Such a composition according to the present invention suitably has (i) a Sun Protection Factor (SPF), measured as herein described, of greater than 10, preferably greater than 15, more preferably greater than 20, particularly greater than 25, and especially greater than 30, and generally up to 60, and/or (ii) a UVA Protection Factor (UVA PF) measured as herein described, of greater than 3, preferably greater than 5, more preferably greater than 7, particularly greater than 9, and especially greater than 10 and generally up to 20.

The composition suitably has a SPF/UVA PF ratio of less than 6, preferably in the range from 1 to 5, more preferably 1.5 to 4, particularly 2 to 3.5, and especially 2.5 to 3.

A particular surprising feature of the present invention is that the aforementioned SPF, UVA PF, and/or SPF/UVA PF ratio values can be obtained when the titanium dioxide described herein is essentially the only ultraviolet light attenuator present in the composition. By "essentially" is meant less than 3%, preferably less 2%, more preferably less than 1%, particularly less than 0.5%, and especially less than 0.1% by weight based on the total weight of the composition, of any other inorganic and/or organic UV absorber.

The titanium dioxide particles and dispersions of the present invention are useful as ingredients for preparing sunscreen compositions, especially in the form of oil-in-water or water-in-oil emulsions. The compositions may further contain conventional additives suitable for use in the intended application, such as conventional cosmetic ingredients used in sunscreens. As mentioned above, the particulate titanium dioxide as defined herein, may be the only ultra violet light attenuator present, but other sunscreening agents, such as other titanium dioxide, zinc oxide and/or other organic UV absorbers may also be added. For example, the titanium dioxide particles defined herein may be used in combination with other existing commercially available titanium dioxide and/or zinc oxide sunscreens.

The titanium dioxide particles and dispersions of the present invention may be used in combination with organic UV absorbers such as butyl methoxydibenzoylmethane (avobenzone), benzophenone-3 (oxybenzone), 4-methylbenzylidene camphor (enzacamene), benzophenone-4 (sulisobenzone), bis-ethylhexyloxyphenol methoxyphenyl triazine (bemotrizinol), diethylamino hydroxybenzoyl hexyl benzoate, diethylhexyl butamido triazone, disodium phenyl dibenzimidazole tetrasulfonate, drometrizole trisiloxane, ethylhexyl dimethyl PABA (padimate O), ethylhexyl methoxycinnamate (octinoxate), ethylhexyl salicylate (octisalate), ethylhexyl triazone, homosalate, isoamyl p-methoxycinnamate (amiloxate), isopropyl methoxycinnamate, menthyl anthranilate (meradimate), methylene bis-benzotriazolyl tetramethylbutylphenol (bisoctrizole), octocrylene, PABA (aminobenzoic acid), phenylbenzimidazole sulfonic acid (ensulizole), terephthalylidene dicamphor sulfonic acid, and mixtures thereof.

In this specification, the following test methods have been used:

1) Particle Size Measurement of Titanium Dioxide Particles

A small amount of titanium dioxide, typically 2 mg, was pressed into approximately 2 drops of an oil, for one or two minutes using the tip of a steel spatula. The resultant suspension was diluted with solvent and a carbon-coated grid suitable for transmission electron microscopy was wetted with the suspension and dried on a hot-plate. Approximately 18 cm×21 cm photographs were produced at an appropriate, accurate magnification. Generally about 300-500 particles were displayed at about 2 diameters spacing. A minimum number of 300 particles were sized using a transparent size grid consisting of a row of circles of gradually increasing diameter, representing spherical crystals. Under each circle a series of ellipsoid outlines were drawn representing spheroids of equal volume and gradually increasing eccentricity. The basic method assumes log normal distribution standard deviations in the 1.2-1.6 range (wider particle size distributions would require many more particles to be counted, for example of the order of 1000). The suspension method described above was suitable for producing almost totally separated titanium dioxide particles whilst introducing minimal crystal fracture. Any residual aggregates were sufficiently well defined that they, and any small debris, could be ignored, and effectively only individual particles included in the count. Mean length, mean width, mean aspect ratio and size distributions of the titanium dioxide particles were calculated from the above measurements.

2) Crystal Size Measurement of Titanium Dioxide Particles

Crystal size was measured by X-ray diffraction (XRD) line broadening. Diffraction patterns were measured with Cu Kα radiation in a Siemens D5000 diffractometer equipped with an energy dispersive detector acting as a monochromator. Programmable slits were used to measure diffraction from a 12 mm length of specimen with a step size of 0.02°. The data was analysed by fitting the diffraction pattern between 22 and 48° 2θ with a set of peaks corresponding to the reflection positions for rutile and, where anatase was present, an additional set of peaks corresponding to those reflections. The fitting process allowed for removal of the effects of instrument broadening on the diffraction line shapes. The value of mean crystal size was determined for the rutile 110 reflection (at approximately 27.4°2θ) based on its full width at half maximum height (FWHM) using the Scherrer equation, described e.g. in B. E. Warren, "X-Ray Diffraction", Addison-Wesley, Reading, Mass., 1969, pp 251-254.

3) Median Volume Particle Diameter and Particle Size Distribution of Titanium Dioxide Particles in Dispersion i) An organic liquid dispersion of titanium dioxide particles was produced by mixing 5 g of polyhydroxystearic acid with 45 g of C12-C15 alkylbenzoate, and then adding 50 g of titanium dioxide powder into the mixture. The mixture was passed through a horizontal bead mill, operating at 1500 r.p.m. and containing zirconia beads as grinding media for 15 minutes. The dispersion of titanium dioxide particles was diluted to between 30 and 40 g/l by mixing with isopropyl myristate.

ii) An aqueous dispersion was produced by mixing 7 g of oleth-10 (Brij™ O10, ex Croda), 5 g of isodeceth-6 (Synperonic™ 10/6, ex Croda), 0.9 g of phenoxyethanol, 0.5 g simethicone (Silfar S184), 36.6 g of demineralised water, and then adding 50 g of titanium dioxide powder into the mixture. The mixture was passed through a horizontal bead mill, operating at 1500 r.p.m. and containing zirconia beads as grinding media for 65 minutes. The dispersion of titanium dioxide particles was diluted to between 30 and 40 g/l by mixing with a 0.1% by weight aqueous solution of isodeceth-6).

The diluted samples produced in i) or ii) were analysed on the Brookhaven BI-XDC particle sizer in centrifugation mode, and the median volume particle diameter and particle size distribution measured.

4) BET Specific Surface Area of Titanium Dioxide Particles

The BET specific surface area was measured using a Micromeritics Tristar 3000. 1.1 g of each titanium dioxide sample was introduced into sample tubes, degassed for 10 minutes under nitrogen at room temperature, before being heated to 150° C. and held at this temperature for 3 hours, again under nitrogen. The samples were then allowed to cool before being reweighed and the surface area analysed. The gases used for analysis were nitrogen and helium.

5) Change in Whiteness of Titanium Dioxide Particles

A sunscreen formulation (e.g. as in Example 6) was coated on to the surface of a glossy black card and drawn down using a No 2 K bar to form a film of 12 microns wet thickness. The film was allowed to dry at room temperature for 10 minutes and the whiteness of the coating on the black surface ($L_F$) measured using a Minolta CR300 colourimeter.

The change in whiteness ΔL was calculated by subtracting the whiteness of the substrate ($L_S$) from the whiteness of the coating ($L_F$).

6) Photogreying Index

A titanium dioxide mixture was prepared by adding 15 g titanium dioxide to 85 g C12-15 alkyl benzoates, and mixing for 15 minutes using an overhead stirrer. The mixture was passed through a mini-motor mill (Eiger Torrance MK M50 VSE TFV), 75% filled with 0.8-1.2 mm zirconia beads operating at 1500 r.p.m. The freshly milled mixtures were loaded into a 16 mm diameter×3 mm deep recess in 65×30×6 mm acrylic cells. A quartz glass cover slip was placed over the sample to eliminate contact with the atmosphere, and secured in place by a brass catch. Up to 12 cells could be placed on a rotating platform, positioned 12 cm from a 75 W UV light source (Philips HB 171/A with 4 TL29D16/09N lamps) and irradiated for 120 minutes. Sample colour (L*a*b* value) was recorded by a commercial colour meter (Minolta chroma meter CR-300), previously calibrated with a standard white tile (L*=97.95). The change in whiteness ΔL* was calculated by subtracting the whiteness of the substrate before exposure to UV light ($L^*_{initial}$) from the whiteness of the substrate after exposure to UV light. The photogreying index $\Delta L^* = L^*_{(initial)} - L^*_{(120\ min)}$.

7) Sun Protection Factor

The Sun Protection Factor (SPF) of a sunscreen formulation (e.g. as in Example 6) was determined using the in vitro method of Diffey and Robson, J. Soc. Cosmet. Chem. Vol. 40, pp 127-133, 1989.

8) UVA Protection Factor

The UVA Protection Factors ($UVA\ PF_0$ and UVA PF) of a sunscreen formulation (e.g. as in Example 6) were determined as described in COLIPA Guidelines 'Method for In Vitro Determination of UVA Protection Provided by Sunscreen Products Edition of 2007a'. A Labsphere UV-1000S UV transmittance analyzer was used.

A blank (100% transmission) sample was produced by spreading 0.75 mg cm$^{-2}$ (equivalent to 0.02 g) of glycerine onto the roughened surface of a polymethyl methacrylate (PMMA) plate (Helioplates HD2, ex Laboratoire Helios Science Cosmetique).

The sunscreen formulation was applied to the roughened surface of an identical PMMA plate, at a concentration of 0.75 mg cm$^{-2}$ (equivalent to 0.02 g) as a series of small dots distributed evenly across the surface of the plate. Immediately after applying, the formulation was spread over the whole surface of the plate using a latex gloved finger. The coated plate was left to dry in the dark for 15 minutes.

Immediately after drying, a total of 6 UV transmission spectra (290 to 400 nm) were recorded for each plate at different locations. Three different plates were used to give an average of 18 readings of the UV transmission data at each wavelength. The UV-radiation transmitted through the coated plates at each 1 nm increment was quantified. The individual transmission measurements obtained at each wavelength increment were used to calculate an initial UVA protection factor ($UVA\ PF_0$).

Using a long-arc xenon Atlas Suntest CPS+ insolator, the same sunscreen formulation treated plate was then exposed to a single UV dose of simulated sun exposure, which is calculated by the instrument and related to the $UVAPF_0$, after which a second series of transmission measurements were made through the sample. The same number of measurements (i.e. 6×3 plates) were taken as prior to the simulated sun exposure. Again, the transmission values were converted to absorbance values and a post exposure UVA protection factor (UVA PF) was calculated.

9) Extinction Coefficients i) 0.1 g sample of an organic liquid titanium dioxide dispersion was diluted with 100 ml of cyclohexane. This diluted sample was then further diluted with cyclohexane in the ratio sample:cyclohexane of 1:19. The total dilution was 1:20,000.

ii) 0.1 g sample of an aqueous titanium dioxide dispersion was diluted with 100 ml of 0.1% by weight aqueous solution of isodeceth-6 (Synperonic™ 10/6, ex Croda). The total dilution was 1:20,000.

The diluted samples produced in i) or ii) were placed in a spectrophotometer (Perkin-Elmer Lambda 2 UV/VIS Spectrophotometer) with a 1 cm path length and the absorbance, of UV and visible light measured. Extinction coefficients were calculated from the equation $A = E \cdot c \cdot l$, where A=absorbance, E=extinction coefficient in liters per gram per cm, c=concentration in grams per liter, and l=path length in cm.

The invention is illustrated by the following non-limiting examples.

EXAMPLES

Example 1

1 mole of titanium oxydichloride in acidic solution was reacted with 3 moles of NaOH in aqueous solution. After the initial reaction period, the temperature was increased to above 70° C., and stirring continued. The reaction mixture was neutralised by the addition of aqueous NaOH, and allowed to cool below 70° C. After filtering, approximately 400 g of the resulting filter cake which contained 60% by weight of water was calcined using a Carbolite ESF chamber furnace at 650° C. for 2 hours and ground into a fine powder using an IKA Werke dry powder mill operating at 3,250 rpm. The powder was re-slurried in demineralised water. To the resulting slurry, an alkaline solution of sodium aluminate was added, equivalent to 3.5% by weight $Al_2O_3$ on $TiO_2$ weight, whilst keeping the pH below 11. The temperature was maintained below 60° C. during the addition. The temperature of the slurry was then increased to 75° C., and 4.6% by weight of sodium stearate on $TiO_2$ dissolved in hot water was added. The slurry was equilibrated for 45 minutes and neutralised by adding 20% hydrochloric acid dropwise over 15 minutes, before the slurry was allowed to cool to less than 50° C. The slurry was filtered using a Buchner filter until the cake conductivity at 100 gdm$^{-3}$ in water was <150 μS. The filter cake was oven-dried for 16 hours at 110° C. and ground into a fine powder by an IKA Werke dry powder mill operating at 3,250 rpm.

A dispersion was produced by mixing 5 g of polyhydroxystearic acid with 45 g of C12-C15 alkylbenzoate, and then adding 50 g of dried calcined titanium dioxide powder produced above into the mixture. The mixture was passed through a horizontal bead mill, operating at 1500 r.p.m. and containing zirconia beads as grinding media for 15 minutes.

The titanium dioxide particles or dispersion thereof were subjected to the test procedures described herein, and exhibited the following properties;

(a) Particle size;
i) D (v,0.5)=133 nm,
ii) 10% by volume of particles have volume diameter less than 113 nm,
iii) 16% by volume of particles have volume diameter less than 117 nm, iv) 30% by volume of particles have volume diameter less than 124 nm,
v) 70% by volume of particles have volume diameter less than 146 nm,
vi) 84% by volume of particles have volume diameter less than 170 nm, and
vii) 90% by volume of particles have volume diameter less than 194 nm.
(b) Extinction coefficients;

| $E_{524}$ | $E_{308}$ | $E_{360}$ | E (max) | λ (max) | $E_{308}/E_{524}$ | $E_{360}/E_{524}$ | $E_{360}/E_{308}$ |
|---|---|---|---|---|---|---|---|
| 6.0 | 48.9 | 37.2 | 51.5 | 326 | 8.2 | 6.2 | 0.76 |

(c) BET specific surface area=28.5 $m^2g^{-1}$.
(d) Photogreying index=0.3.

Example 2

A dispersion according to the procedure of Example 1 was produced, except that 4.5 g of polyhydroxystearic acid, 50.5 g of C12-C15 alkylbenzoate, and 45 g of dried calcined titanium dioxide powder were used.
The titanium dioxide dispersion was subjected to the test procedures described herein, and exhibited the following properties;
(a) Extinction coefficients;

| $E_{524}$ | $E_{308}$ | $E_{360}$ | E (max) | λ (max) | $E_{308}/E_{524}$ | $E_{360}/E_{524}$ | $E_{360}/E_{308}$ |
|---|---|---|---|---|---|---|---|
| 6.6 | 47.6 | 38.4 | 50.6 | 326 | 7.2 | 5.8 | 0.81 |

Example 3

Titanium dioxide particles were produced according to the procedure of Example 1, except that no alumina/stearate coating was applied.
A dispersion was produced according to the procedure of Example 1, except that 1.68 g of polyhydroxystearic acid, 1.68 g of isostearic acid, 51.64 g of C12-C15 alkylbenzoate, and 45 g of dried calcined titanium dioxide powder produced above were used.
The titanium dioxide dispersion was subjected to the test procedures described herein, and exhibited the following properties;
(a) Extinction coefficients;

| $E_{524}$ | $E_{308}$ | $E_{360}$ | E (max) | λ (max) | $E_{308}/E_{524}$ | $E_{360}/E_{524}$ | $E_{360}/E_{308}$ |
|---|---|---|---|---|---|---|---|
| 6.3 | 47.1 | 38.2 | 50.6 | 328 | 7.4 | 6.1 | 0.82 |

Example 4

A dispersion was produced by mixing 110 g of polyhydroxystearic acid and 790 g of C12-C15 alkylbenzoate, and then adding 1100 g of dried calcined titanium dioxide powder produced in Example 1 to the mixture, using a Greaves ST-C-DC mixer. The mixture was then milled using a Netzsch Labstar horizontal bead mill, with a power input of 0.55 kWh/kg, operating at 2600 rpm and containing zirconia beads as grinding media.
The titanium dioxide dispersion was subjected to the test procedures described herein, and exhibited the following properties;
(a) Extinction coefficients;

| $E_{524}$ | $E_{308}$ | $E_{360}$ | E (max) | λ (max) | $E_{308}/E_{524}$ | $E_{360}/E_{524}$ | $E_{360}/E_{308}$ |
|---|---|---|---|---|---|---|---|
| 5.2 | 47.6 | 34.4 | 49.1 | 321 | 9.1 | 6.6 | 0.72 |

Example 5

An aqueous dispersion was produced by mixing 7 g of oleth-10 (Brij™ O10, ex Croda), 5 g of isodeceth-6 (Synperonic™ 10/6, ex Croda), 0.9 g of phenoxyethanol, 0.5 g simethicone (Silfar S184), 36.6 g of demineralised water, and then adding 50 g of dried calcined titanium dioxide powder produced in Example 1. The mixture was passed through a horizontal bead mill, operating at 1500 r.p.m. and containing zirconia beads as grinding media for 65 minutes.

Example 6

The titanium dioxide dispersion produced in Example 2 was used to prepare sunscreen emulsion formulations F1 and F2 having the following composition;

| Trade Name | INCI Name | F1 % w/w | F2 % w/w |
|---|---|---|---|
| Phase A. | | | |
| Arlacel ™ 165 FI (ex Croda) | Glyceryl Stearate (and) PEG-100 Stearate | 6 | 6 |
| Span ™ 60 (ex Croda) | Sorbitan Stearate | 0.5 | 0.5 |
| Tween ™ 60 (ex Croda) | Polysorbate 60 | 2.7 | 2.7 |
| Stearyl Alcohol | Stearyl Alcohol | 1 | 1 |
| Light Mineral Oil | Mineral Oil | 8 | 4 |
| Crodamol ™ OP (ex Croda) | Ethylhexyl Palmitate | 2.5 | 2.5 |
| DC 200 350 cps | Dimethicone | 2 | 2 |
| Unimer U-15 (ex Induchem) | VP/Eicosene Copolymer | 1 | 1 |
| TiO₂ dispersion | | 22 | 33 |
| Phase B. | | | |
| Water | Aqua | 49.2 | 42.2 |
| Keltrol RD | Xanthan Gum | 0.1 | 0.1 |
| Propylene Glycol | Propylene Glycol | 4 | 4 |
| Phase C. | | | |
| Germaben II | Propylene Glycol, Diazolidinyl Urea, Methylparaben, Propylparaben | 1 | 1 |

Procedure
1. Keltrol RD was dispersed into water, and the remaining water Phase A ingredients added to the mixture, which was heated to 65-80° C.
2. The oil Phase B ingredients were combined and heated to 75-80° C.
3. The oil phase was added to the water phase with stirring.
4. The mixture was homogenised for 2 minutes.
5. The resulting emulsion was cooled to room temperature with stirring, with the Phase C preservative being added below 40° C.

The formulations were subjected to the test procedures described herein, and exhibited the following properties;

|  | F1 | F2 |
|---|---|---|
| i) SPF | 23.8 | 40.6 |
| ii) Label SPF* | 20 | 30 |
| iii) UVA $PF_0$ | 8.3 | 10.3 |
| iv) UVA PF | 8.0 (9.9 $Jcm^{-2}$)+ | 10.0 (12.4 $Jcm^{-2}$)+ |
| v) SPF/UVA $PF_0$ | 2.9 | 4.0 |
| vi) SPF/UVA PF | 3.0 | 4.1 |
| vii) Label SPF/UVA PF | 2.5 | 3.0 |
| viii) ΔL | 14.2 | 22.6 |

*According to EU recommendations for labelling of sunscreens, 22 Sep. 2006
+UV dose applied.

Example 7

Titanium dioxide particles were produced according to the procedure of Example 1, except that approximately 400 kg of filter cake which contained 60% by weight of water was calcined for 8 hours at 650° C. in a static kiln. After alumina/stearate coating as described in Example 1, the resultant slurry was filtered using a filter press until the wash-water conductivity was <150 μS. The filter cake was spray dried and ground into a fine powder.

A dispersion was produced by mixing 12.5 kg of polyhydroxystearic acid with 89.7 kg of C12-C15 alkylbenzoate, and then adding 124.9 kg of dried calcined titanium dioxide powder produced above into the mixture. The mixture was passed through a horizontal bead mill containing zirconia beads as grinding media.

The titanium dioxide dispersion was subjected to the test procedures described herein, and exhibited the following properties;
(a) Particle size;
i) D (v,0.5)=143 nm,
ii) 10% by volume of particles have volume diameter less than 80 nm,
iii) 16% by volume of particles have volume diameter less than 102 nm,
iv) 30% by volume of particles have volume diameter less than 122 nm,
v) 70% by volume of particles have volume diameter less than 168 nm,
vi) 84% by volume of particles have volume diameter less than 197 nm, and
vii) 90% by volume of particles have volume diameter less than 220 nm.
(b) Extinction coefficients;

| $E_{524}$ | $E_{308}$ | $E_{360}$ | E (max) | λ (max) | $E_{308}/E_{524}$ | $E_{360}/E_{524}$ | $E_{360}/E_{308}$ |
|---|---|---|---|---|---|---|---|
| 8.6 | 43.0 | 35.9 | 43.5 | 323 | 5.0 | 4.2 | 0.83 |

Example 8

A dispersion according to the procedure of Example 7 was produced, except that 14.0 kg of polyhydroxystearic acid, 100.7 kg of C12-C15 caprylic/capric triglyceride, and 140.3 kg of dried calcined titanium dioxide powder were used.

The titanium dioxide dispersion was subjected to the test procedures described herein, and exhibited the following properties;
(a) Extinction coefficients;

| $E_{524}$ | $E_{308}$ | $E_{360}$ | E (max) | λ (max) | $E_{308}/E_{524}$ | $E_{360}/E_{524}$ | $E_{360}/E_{308}$ |
|---|---|---|---|---|---|---|---|
| 8.8 | 44.6 | 38.6 | 46.6 | 330 | 5.1 | 4.3 | 0.87 |

Example 9

(a) The titanium dioxide dispersion produced in Example 7 was used to prepare a sunscreen emulsion formulation having the following composition;

| Trade Name | INCI Name | % w/w |
|---|---|---|
| Phase A. | | |
| Cithrol™ DPHS (ex Croda) | PEG-30 Dipolyhydroxystearate | 2.5 |
| Crodamol™ AB (ex Croda) | C12-15 Alkyl benzoate | 13 |
| Arlamol™ HD (ex Croda) | Isohexadecane | 3 |
| Arlamol™ PS15E (ex Croda) | PPG-15 Stearyl Ether | 1 |
| Xiameter PMX-245 | Cyclopentasiloxane | 2 |
| TiO₂ dispersion | | 12 |
| Phase B. | | |
| Water | Aqua | 60.2 |
| Magnesium Sulphate Heptahydrate | Magnesium Sulphate Heptahydrate | 0.8 |
| Pricerine™ 9091 (ex Croda) | Glycerin | 4.5 |
| Phase C. | | |
| Germaben II | Propylene Glycol, Diazolidinyl Urea, Methylparaben, Propylparaben | 1 |

Procedure
1. The oil Phase A ingredients, except for the TiO₂ dispersion, were combined and heated to 85° C.
2. The water Phase B ingredients were combined and heated to 85° C.
3. The TiO₂ dispersion was added to the oil phase with stirring whilst maintaining the temperature.
4. The water phase was added to the oil phase slowly, with intensive stirring.
5. The mixture was homogenised for one minute.
6. The resulting emulsion was cooled to room temperature with stirring, with the Phase C preservative being added below 40° C.

(b) The titanium dioxide dispersion produced in Example 8 was used to prepare a sunscreen emulsion formulation having the following composition;

| Trade Name | INCI Name | % w/w |
|---|---|---|
| Phase A. | | |
| Arlacel™ 1690 (ex Croda) | Sorbitan Isostearate (and) Polyglyceryl-3 Polyricinoleate) | 3.5 |
| Prisorine™ 3515 (ex Croda) | Isostearyl Alcohol | 2 |
| Organic Jojoba Oil | Simmondsia Chinensis Oil | 5 |
| Organic Coconut Oil | Cocos Nucifera Oil | 5 |
| Pripure™ 3759 (ex Croda) | Squalane | 2 |
| Candelilla Wax | Euphorbia Cerifera (Candelilla) Wax | 0.5 |
| Dermosoft PEA eco | Phenethyl Alcohol | 0.8 |
| TiO₂ dispersion | | 24 |

-continued

| Trade Name | INCI Name | % w/w |
|---|---|---|
| Phase B. | | |
| Water | Aqua | 52.1 |
| Sodium Chloride | Sodium Chloride | 4 |
| Keltrol RD | Xanthan Gum | 0.7 |
| Pricerine ™ 9091 (ex Croda) | Glycerin | 0.1 |
| Phase C. | | |
| Dermofeel Toco 70 Non-GMO | Tocopherol | 0.3 |

Procedure

1. The oil Phase A ingredients, except for the $TiO_2$ dispersion, were combined and heated to 85° C.
2. The water Phase B ingredients were combined and heated to 85° C.
3. The $TiO_2$ dispersion was added to the oil phase with stirring whilst maintaining the temperature.
4. The water phase was added to the oil phase with fast stirring.
5. The mixture was homogenised for one minute.
6. The resulting emulsion was cooled to room temperature with stirring, with the Phase C preservative being added below 40° C.

The formulations were subjected to the test procedures described herein, and exhibited the following properties;

| | (a) | (b) |
|---|---|---|
| i) SPF | 19 | 38 |
| ii) Label SPF* | 15 | 30 |
| iii) UVA $PF_0$ | 6 | 13 |
| iv) UVA PF | 6 (10.4 $Jcm^{-2}$)+ | 13 (16.5 $Jcm^{-2}$)+ |
| v) SPF/UVA $PF_0$ | 3.2 | 2.9 |
| vi) SPF/UVA PF | 3.2 | 2.9 |
| vii) Label SPF/UVA PF | 2.5 | 2.3 |

*According to EU recommendations for labelling of sunscreens, 22 Sep. 2006
+UV dose applied.

The above examples illustrate the improved properties of a particulate titanium dioxide, dispersion, and/or sunscreen product according to the present invention.

The invention claimed is:

1. A particulate titanium dioxide having:
   i) an E524 of less than 9 l/g/cm, an E360 of 25 to 50 l/g/cm, and an E360/E308 ratio of 0.5 to 1.0;
   ii) a median volume particle diameter of 85 to 175 nm, as measured by a particle sizer in centrifugation mode using X-ray detection;
   iii) a BET specific surface area in a range from 22 to 40 $m^2g^{-1}$; and
   iv) a mean aspect ratio of 1.2 to 2.0:1.
2. The titanium dioxide according to claim 1 wherein the median volume particle diameter is 100 to 160 nm.
3. The titanium dioxide according to claim 1 having a mean length of 30 to 75 nm and a mean aspect ratio of 1.3 to 1.8:1.
4. A dispersion comprising a dispersing medium and particulate titanium dioxide as defined in claim 1.
5. The dispersion according to claim 4 comprising at least 30% by weight of the titanium dioxide particles.
6. The dispersion according to claim 4, wherein the dispersing medium is an organic liquid.
7. A sunscreen product comprising the titanium dioxide particles as defined in claim 1.
8. The sunscreen product of claim 7, wherein the sunscreen product has an SPF/UVA PF ratio in a range from 1 to 5.
9. The sunscreen product of claim 7, wherein the defined titanium dioxide particles are essentially the only ultraviolet light attenuator present.
10. A sunscreen product comprising the dispersion of claim 4.
11. The sunscreen product of claim 10, wherein the sunscreen product has an SPF/UVA PF ratio in a range from 1 to 5.
12. The sunscreen product of claim 10, wherein the defined titanium dioxide particles are essentially the only ultraviolet light attenuator present.
13. A particulate titanium dioxide having:
   i) an E524 of less than 9 l/g/cm, an E360 of 25 to 50 l/g/cm, and an E360/E308 ratio of 0.5 to 1.0;
   ii) a median volume particle diameter of 115 to 150 nm, as measured by a particle sizer in centrifugation mode using X-ray detection;
   iii) a BET specific surface area in a range from 22 to 40 $m^2g^{-1}$; and
   iv) a mean aspect ratio of 1.2 to 2.0:1.
14. A particulate titanium dioxide having:
   i) an E524 of less than 9 l/g/cm, an E360 of 25 to 50 l/g/cm, and an E360/E308 ratio of 0.5 to 1.0;
   ii) a median volume particle diameter of 125 to 140 nm, as measured by a particle sizer in centrifugation mode using X-ray detection;
   iii) a BET specific surface area in a range from 22 to 40 $m^2g^{-1}$; and
   iv) a mean aspect ratio of 1.2 to 2.0:1.
15. The titanium dioxide according to claim 2 having a mean length of 30 to 75 nm and a mean aspect ratio of 1.3 to 1.8:1.
16. The titanium dioxide according to claim 13 having a mean length of 30 to 75 nm and a mean aspect ratio of 1.3 to 1.8:1.
17. The titanium dioxide according to claim 14 having a mean length of 30 to 75 nm and mean aspect ratio of 1.3 to 1.8:1.
18. The titanium dioxide according to claim 1 having a mean aspect ratio of 1.4 to 1.6:1.
19. The titanium dioxide according to claim 2 having a mean aspect ratio of 1.4 to 1.6:1.
20. The titanium dioxide according to claim 13 having a mean aspect ratio of 1.4 to 1.6:1.
21. The titanium dioxide according to claim 14 having a mean aspect ratio of 1.4 to 1.6:1.

* * * * *